(12) United States Patent
Kindlein (10) Patent No.: US 7,016,471 B2
(45) Date of Patent: Mar. 21, 2006

(54) MINIATURE X-RAY SOURCE DEVICE

(75) Inventor: Johann Kindlein, Toenisvorst (DE)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 10/878,160

(22) Filed: Jun. 29, 2004

(65) Prior Publication Data

US 2005/0031083 A1    Feb. 10, 2005

(30) Foreign Application Priority Data

Jun. 30, 2003    (EP) ................................. 03077041

(51) Int. Cl.
*H01J 35/06* (2006.01)
(52) U.S. Cl. ...................... 378/136; 378/123
(58) Field of Classification Search ................ 378/123, 378/122, 136, 121, 137, 138, 119
See application file for complete search history.

(56) References Cited

U.S. PATENT DOCUMENTS

| | | | |
|---|---|---|---|
| 3,322,993 A | | 5/1967 | Vinopal |
| 5,729,583 A | * | 3/1998 | Tang et al. ................. 378/122 |
| 5,838,761 A | | 11/1998 | Behner et al. |
| 6,134,300 A | * | 10/2000 | Trebes et al. ............... 378/136 |
| 6,353,658 B1 | * | 3/2002 | Trebes et al. ............... 378/123 |
| 6,438,206 B1 | * | 8/2002 | Shinar et al. ............... 378/123 |
| 6,477,235 B1 | * | 11/2002 | Chornenky et al. ......... 378/143 |
| 6,553,096 B1 | * | 4/2003 | Zhou et al. ................. 378/122 |
| 2002/0063500 A1 | | 5/2002 | Keren | 
| 2003/0090202 A1 | * | 5/2003 | Gallitognotta et al. ...... 313/558 |

FOREIGN PATENT DOCUMENTS

| | | |
|---|---|---|
| EP | 0 860 180 A2 | 8/1998 |
| EP | 0 860 181 A2 | 8/1998 |
| JP | 2000-208294 A | 7/2000 |
| WO | WO 01/18842 A1 | 3/2001 |
| WO | WO 02/102459 A1 | 12/2002 |

\* cited by examiner

*Primary Examiner*—David V. Bruce
*Assistant Examiner*—Hoon Song
(74) *Attorney, Agent, or Firm*—Birch, Stewart, Kolasch & Birch, LLP (57) ABSTRACT

A miniature X-ray source device connected to a distal end of a guiding wire for insertion towards a desired location within an animal body for effecting radiation thereby. The X-ray source device at least includes a vacuum tube containing a cathode and an anode spaced apart at a distance from each other; an emitter for emitting free electrons from the cathode; an electric field generator for applying a high-voltage electric field between the cathode and the anode for accelerating the emitted free electrons towards the anode; and a getter material located in a high-voltage electric field free region in the vacuum tube. The vacuum tube is at least partly transparent to X-ray radiation emitted by the anode.

24 Claims, 7 Drawing Sheets

Fig. 1

PRIOR ART

MINIATURE X-RAY SOURCE DEVICE

This Non-provisional application claims priority under 35 U.S.C. § 119(a) on Patent Application No(s). 03077041.6 filed in Europe on Jun. 30, 2003, the entire contents of which are hereby incorporated by reference.

The invention relates to a miniature X-ray source device connected to a distal end of a guiding wire for insertion towards a desired location within an animal body for effecting radiation therapy, said X-ray source device at least comprising:

a vacuum tube containing a cathode and an anode spaced apart at some distance from each other;

emitting means for emitting free electrons from the cathode;

electric field generating means for applying during use a high-voltage electric field between said cathode and said anode for accelerating said emitted free electrons towards said anode;

a getter material located in a high-voltage electric field free region in said vacuum tube; wherein said vacuum tube being at least partly transparent to X-ray radiation emitted by said anode.

The present invention relates to a generation of X-rays for medical purposes, and in particular it relates to miniature X-ray source device for intravascular treatment of lesions in body tissue, in particular for treatment of stenosis in coronary vessels and the treatment of cancer tumours.

Radiation therapy is a well-established method for treatment of several diseases, including cancer. The presumptive usefulness of a miniature X-ray source device is clear. The insertion of such a source device into vessels or other body cavities would allow the delivered radiation dose to be confide to a small tissue region. More specific, a catheter with a miniaturized X-ray source device could be used for irradiation of cardiovascular tissue.

Such miniature X-ray source device is for example known from the International Patent Application No. WO 01/18842 A1. In this patent publication a miniature X-ray source device is disclosed having a compact vacuum tube assembly containing a cathode and an anode positioned within said vacuum tube at some distance from each other, means for generating a high-voltage electric field between the anode and cathode for delivering a high-voltage to the anode and a getter material disposed within said vacuum tube for maintaining a required vacuum level necessary for a proper operation of the X-ray source device.

The X-ray source device operates by applying a high-voltage between the anode and the cathode in order to accelerate free electrons emitted by said cathode towards the anode. Due to this accelerating high-voltage electric field between the cathode and anode the electrons impact on the anode with a significant high velocity and create in said anode material X-ray irradiation having a significant high energy level through collisional excitation of the atoms within the anode material. The X-ray radiation is emitted from said vacuum tube towards the patient's tissue surrounding the X-ray source device in order to treat for example cancer tumours by means of radiation therapy treatment.

In order to assure an efficient acceleration of the free electrons emitted from said cathode towards the anode a significantly low vacuum level within the vacuum tube is required. A significant low vacuum level is also necessary to prevent a gas discharge of the gas molecules still present in said vacuum tube or to avoid the forming of an electrical arc within said vacuum tube. Further a total destruction of the assembly is also possible.

In order to avoid these problems the known miniature X-ray source device is provided with a getter material, which is positioned within the vacuum tube and preferably at a location away from the influence of the high-voltage electric field applied between the anode and cathode. The know getter material has an activation temperature at which it will react with stray gas molecules within the vacuum tube of the X-ray source device. For example, the SAES ST 707 alloy getter has an activation temperature of 400°–500° C. The alloy is composed of 24.6% vanadium, 5.4% iron, 70% zirconium.

Before the getter material is activated, it is covered with an oxidation layer that shields the getter material from the atmosphere at the normal conditions. When the getter material is heated to its activation temperature in a vacuum, the oxidation layer diffuses into the interior of the getter material, revealing the active getter surface, which will react and bond with any stray gas molecule still present within the vacuum. The getter, therefore, eliminates stray gas molecules, thereby improving the quality of the vacuum level within the vacuum tube up to $10^{-7}$ to $10^{-8}$ Torr.

However it is necessary to locate the getter material inside the vacuum tube at a location where no electric field between the anode and cathode exits. An essentially electric field free location of the getter material is required as therefore the getter would not present any internal electrical problems associated with surface arcing or breakdown.

To this end, in order to benefit from the use of a getter material inside the vacuum tube for improving the vacuum level inside as well as avoiding any electrical problems as mentioned above and to obtain an improved miniature X-ray tube source device having reduced constructional dimensions according to the invention said cathode is arranged for shielding said getter material from said high-voltage electric field.

With these features it is possible to position the getter material inside the vacuum tube, wherein it is shielded off from said high-voltage electric field by means of the cathode. A significant reduction in the constructional dimensions is thus obtained, allowing a further miniaturisation of the known miniature X-ray source device thus further improving the positioning of such X-ray source device within the patient's body.

According to a further aspect of the invention said cathode is placed between said getter material and said anode, wherein further said cathode is at least partly covering said getter material.

In a preferred embodiment exhibiting a more efficient use of the inner space of the vacuum tube the miniature X-ray source device according to the invention is characterized in that said cathode has an elongated shape with a polygonal cross-section and that said getter material is disposed within said cathode said getter material is supported by said cathode and electrically isolated from it. These latter features assure a complete electrically isolated getter material within the cathode according to the Principle of Faraday's Cage.

In another embodiment said elongated shaped cathode has a circular or oval cross-section.

In all these embodiments said getter material may be rod-shaped.

These features significantly reduce the constructional dimensions of the vacuum tube and hence of the miniature X-ray source device, improving the insertion and displacement of such device in a patient's body. Also the occurrence of any internal electrical problems are herewith avoided. Furthermore with these embodiments a significant enlargement of the getter material surface is obtained resulting in an improved capacity for eliminating stray gas molecules still present in the vacuum tube.

In order to ensure a proper contact between the getter material and the vacuum chamber within the vacuum tube according to a preferred embodiment said cathode is provided with at least one opening wherein in a more sophisticated embodiment said cathode is made from a grating material.

A more robust construction is obtained as in an advantageous embodiment said getter material is supported by said cathode.

In a further embodiment of the miniature X-ray source device according to the invention said cathode is of a field emission type having a ferro-electric electron emitting material.

Preferably said ferro-electric electron emitting material is positioned between a lower electrode and an upper electrode, both electrodes being connected to a driving voltage, wherein in one embodiment said upper electrode is constructed as an electrically conductive sheet provided with a large number of openings serving as emitting holes for the emitted free electrons.

In another advantageous embodiment said upper electrode is constructed as at least one electrically conductive frame in which with a large number disc shaped elements is fixed on said ferro-electric electron emitting material.

In another embodiment the electron emitting material is of a cold cathode type formed from carbon nanotubes. In the embodiment wherein the cathode is a so-called cathode type formed from carbon nanotubes, carbon nanotubes are aligned mono-wall nanotubes or carbon nanotubes are aligned multi-wall nanotubes. In both embodiments said carbon nanotubes may be randomised nanotubes.

In contrast to radioactive sources a miniature X-ray source device would be switchable on and off electronically. Furthermore the energy of its radiation would be given by the voltage between the electrodes. As the penetration depth of X-rays in tissue depends on the X-ray energy the optimal depth could be obtained by applying the corresponding electrode voltage.

In particular in brachytherapy treatments radioactive treatment sources are implanted towards a desired location within the patient's body. Said radioactive treatment sources, for example consisting of Ir-192 sources emit radiation following the principle of natural radioactive decay. However the use of a radioisotope as an energy emitting source for performing radiation therapy inside a patient's body, like an Ir-192 source exhibits certain drawbacks as regard to handling, storing of the radioactive treatment source at the time of performing the radiation therapy as well as regard to the disposal of the radioactive material after use. Furthermore the use of radioactive treatment sources require extreme care in order to avoid the hazardous exposure of the medical personal and patient to radioactive irradiation.

A further aspect of the present invention aims to overcome these drawbacks connected with the use of radioactive sources for performing radiation therapy treatments and intends to provide a miniature X-ray source device having a radiation dose distribution similar to that of a cylindrical radioactive treatment source, for example of an Ir-192 radiation treatment source.

According to the invention the miniature X-ray source device is characterized in that vacuum tube comprises a distal end face, the inner surface of said distal end face also being provided with said anode material, and wherein a part of said electron emitting material of said cathode is facing said distal end face.

With these features the radiation of this new type of miniature X-ray source device is emitted on the overall outer surface of the vacuum tube and not only through a limited area. With the X-ray source device according to the invention an X-ray radiation dose distribution is obtained which is similar to that of a radioactive treatment source, such as a Ir192 radiation treatment source.

In this specific embodiment according to the invention the cathode is tubular shaped having a distal free end provided with electron emitting material directed towards said distal end face of said vacuum tube, and more in particular the electron emitting surface of said cathode conforms to the inner surface of said vacuum tube being covered with said anode material.

In an advantageous embodiment which more accurately conforms the dose distribution of a radioactive treatment source according to the invention said distal end face of said vacuum tube and said distal free end of said cathode are semi-spherically shaped.

A more homogeneous X-ray radiation dose distribution is obtained as according to the invention said distal end face of said vacuum tube and said distal free end of said cathode are equally spaced apart form each other.

The invention will now be described with reference to a drawing which drawing shows.

Figure 1:
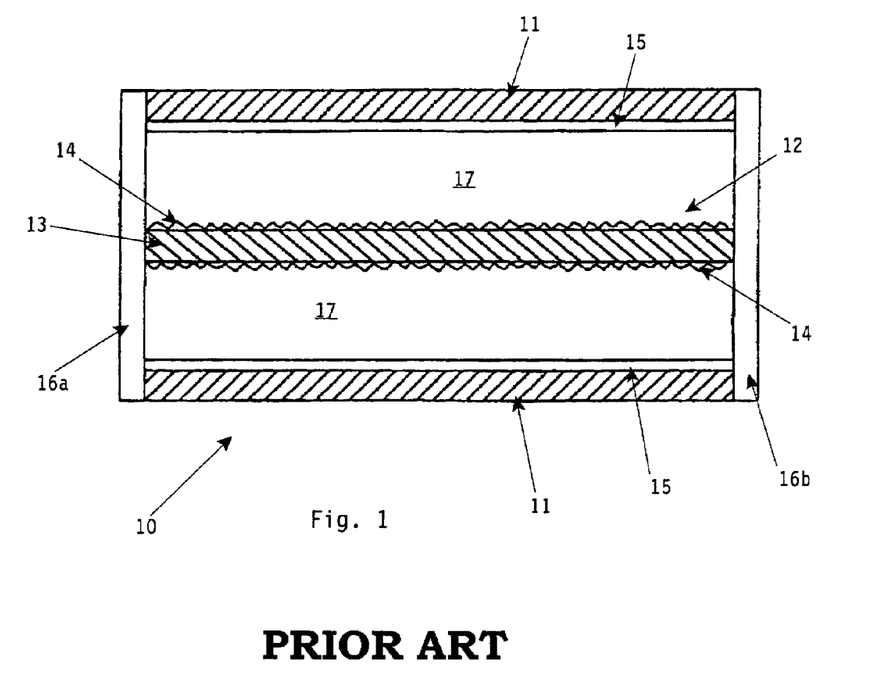
FIG. 1 discloses a miniature X-ray source device according to the state of the art.

In FIG. 1 a known miniature X-ray source device according to the state of the art is disclosed showing the miniature X-ray source device in a longitudinal cross-section. The miniature X-ray source device according to the prior art comprises an elongated member 13 such as a rod or a wire. This elongated member acts as a support for a thin film cathode depicted with reference numeral 14, covering the outer surface of the thin elongated member 13. The assembly consisting of the elongated rod 13 and the cathode 14 is accommodated in an elongated, cylindrically shaped housing 11 which forms a cavity or vacuum tube 17. The inner surface of the vacuum tube wall 11 is provided with an anode material 15.

The cathode material 14 consist of an electron emitting material from which electrons are freed using techniques already known in the art.

Although not shown in FIG. 1 in general a known miniature X-ray source device according to the state of the art is further provided with means for establishing a high-voltage electric field between the anode and cathode. To this end the anode material is connected with an supply wire connected with a high-voltage source.

The electrons freed from said cathode material are accelerated by said high-voltage electric field and impact on the anode material. Due to the high velocity of the electrons specific X-ray radiation is generated within the anode material. The X-ray radiation will escape the vacuum tube 11 towards the tissue of the patient in which the miniature X-ray source device is implanted due to the fact that the vacuum tube 11 is manufactured from a material which is highly transparent for X-ray radiation.

With this configuration a X-ray radiation dose distribution is generated which is cylindrically shaped seen in a plane perpendicular to the longitudinal axis of the support member 13 of the cathode 14.

As stated in the introduction of this patent application the radiation dose distribution thus generated is not always applicable for certain radiation therapy treatments, for example brachytherapy.

Figures 2A, 2B:
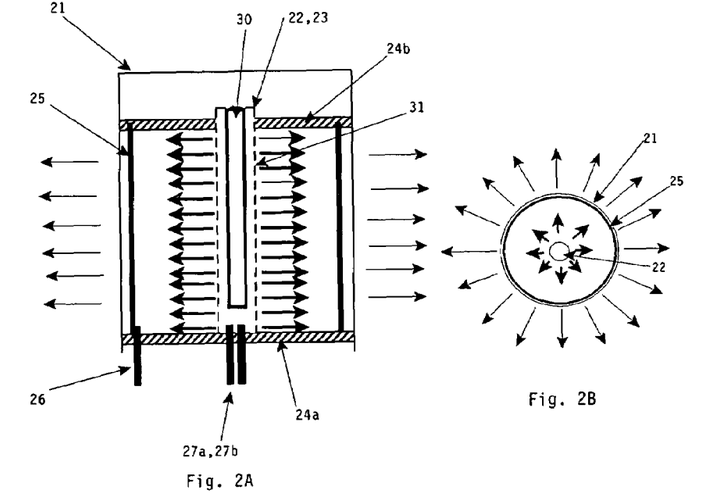
FIG. 2a–2c disclose three different embodiments of a first aspect of a miniature X-ray source device according to the invention.
Figure 2C:
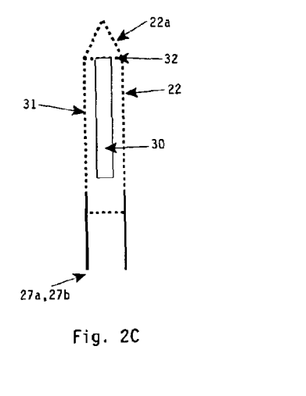

In FIG. 2a–2c a first aspect of a miniature X-ray source device according to the invention is disclosed. The miniature X-ray tube 20 as shown in FIG. 2a comprises a vacuum tube 21 provided on its inner surface with an anode material 25. Within said vacuum tube 21 an elongated cathode 22 is accommodated, which cathode 22 is concentrically positioned within the vacuum tube 21. The elongated cathode support 22 is provided with cathode material 23 (electron emitting material).

The elongated cathode 22, 23 is mounted within the vacuum tube 21 using two support members 24a–24b which maintain the cathode 22, 23 in an electrically isolated and concentrically manner within the vacuum tube. Furthermore the support member 24a has a sealing function in order to maintain a proper vacuum level within the vacuum tube. Furthermore the anode 25 is connected to a high-voltage supply line 26 for establishing a high-voltage electric field between the anode and the cathode.

Likewise free electrons emitted from said electron emitting material 23 of the cathode 22 are accelerated in the direction of the anode material 25 (see the arrows) and upon impact on said anode material specific X-ray radiation is generated. Said X-ray radiation leaves through the vacuum tube 21 made of a highly transparent material for X-ray radiation towards the tissue of the patient in which the miniature X-ray source device is implanted for performing a radiation therapy treatment, for example treatment of cancer cells.

According to said first aspect of the invention the cathode 22 is arranged for shielding off a getter material 30 from the high-voltage electric field existing between the cathode and the anode 21 of the miniature X-ray source device as disclosed in FIGS. 2a–2c. The getter material is rod-shaped and electrically isolated accommodated in a hollow cathode 22. which cathode is tubular shaped and provided preferably with at least one opening 31. The opening 31 ensures a proper vacuum connection between the getter material 30 and the cavity 17 of the vacuum tube 21 in order to eliminate or capture stray gas molecules still present in the cavity 17 of the vacuum tube 21. Therefore the use of the getter material guarantees a low vacuum level within the vacuum tube 21 necessary for a proper operation of the miniature X-ray source device according to the invention.

Although one opening provided in the tubular hollow shaped cathode 22 suffices for a proper functioning of the getter material 30 it is preferred to provide the cathode with multiple openings 31 and in a specific embodiment said cathode 22 is made of a grating material exhibiting a large number of openings.

In FIG. 2b schematically the radiation dose distribution of a miniature X-ray source device according to the invention is disclosed. Not only a radiation dose distribution about 360° in a plane perpendicular to the longitudinal direction of the X-ray source device is obtained but also radiation in longitudinal direction of the miniature X-ray source device is emitted.

Figure 3A:
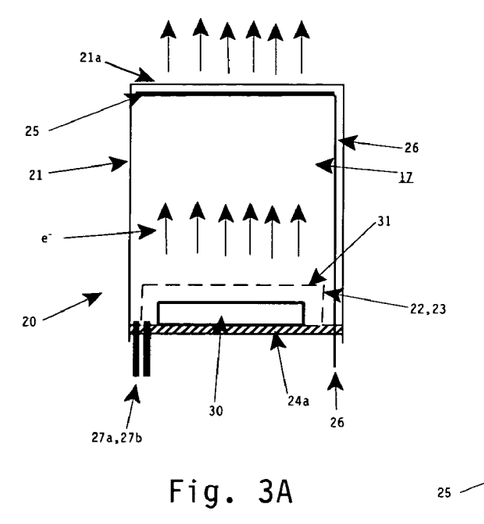
FIG. 3a–3c disclose three other embodiments of said first aspect of a miniature X-ray source device according to the invention.
Figure 3B:
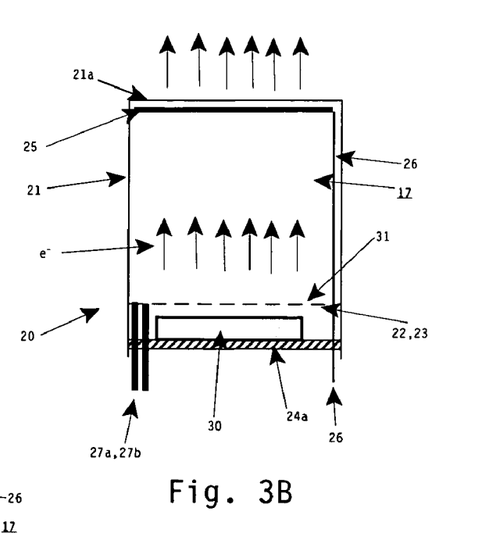
Figure 3C:
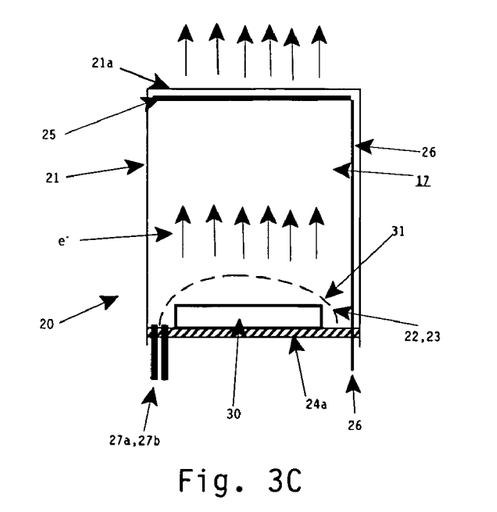

In FIGS. 3a–3c are three other embodiments of a miniature X-ray tube according to the invention disclosed. In the FIGS. 3a–3c the corresponding components/parts are marked with the same reference numerals as in FIGS. 2a–2c.

In the FIGS. 3a–3c specific configurations are shown of the cathode 22, 23 shielding off the getter material 30 electrically isolated from the high-voltage electric field present between the cathode 22, 23 and the anode 25. Here the vacuum tube has a different construction with respect to the embodiments shown in FIGS. 2a–2c, as here the vacuum tube 21 is provided with a distal end face 21b where the anode 25 is positioned. The X-ray radiation generated within the anode leaves the vacuum tube 21 via said distal end face 21a being at least partly transparent for X-ray radiation.

The cathode 22, 23 is mounted on the support member 24a sealing the vacuum tube from the outer atmosphere. The cathode 22, 23 is according to invention arranged in shielding off a getter 30 also mounted to said support member 24a.

In all three embodiments the cathode 22, 23 is preferably made from a grating material provided with at least one opening 31 allowing the getter of being into contact with the vacuum in order to eliminate any stray gas molecule within the cavity 17.

Figure 4A:
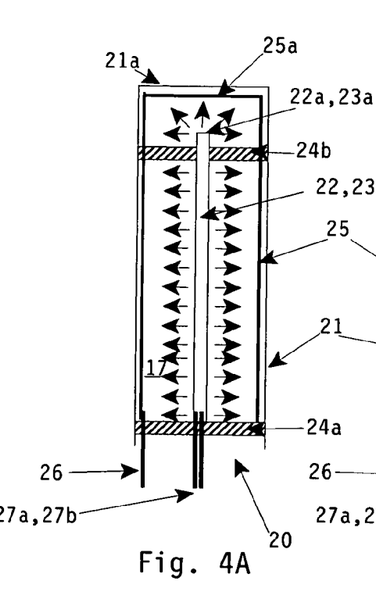
FIG. 4a–4c disclose three other embodiments of a further aspect of a miniature X-ray source device according to the invention.
Figure 4B:
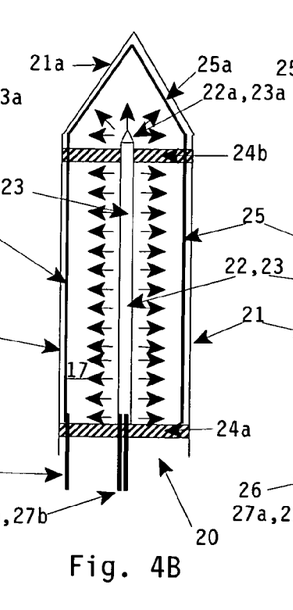
Figure 4C:
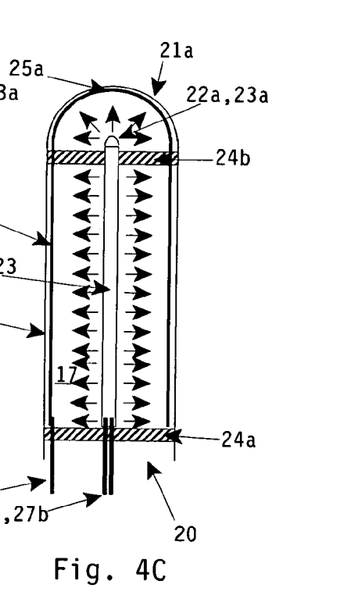

In FIGS. 4a–4c are three other embodiments of a miniature X-ray tube according to the invention disclosed. Also in the FIGS. 4a–4c the corresponding components/parts are marked with the same reference numerals as in FIGS. 2a–2c, 3a–3c.

According to a further aspect of the invention in FIG. 4a the vacuum tube 21 comprises a distal end face 21a also being provided with anode material 25a and said elongated cathode 22 is provided with a distal end 22a which distal end 22a is provided with electron emitting material 23a and said part of 23a of said electron emitting material 23 is facing said distal end face 21a of said vacuum tube 21 provided with said additional anode material 25a.

Hence with this configuration a X-ray radiation dose distribution is obtained having a more spatial characteristic resulting in a more complete and accurate coverage of the tissue directly surrounding the miniature X-ray source device as implanted inside a patient's body.

In FIG. 4b another embodiment of a miniature X-ray source device according to the invention is disclosed wherein said distal end face of the vacuum tube 21 exhibits a frustoconical (pyramid) shape resulting in a different spatial X-ray radiation distribution. Furthermore in FIG. 4b also the distal end of the cathode 22 has a shape which is conformal to the shape of the distal end face 21a of the vacuum tube 21.

In FIG. 4c is another embodiment of a X-ray source device according to the invention disclosed wherein the cathode 22 is provided with a rounded distal end 22a having a semi-spherical shape. Likewise the distal end face 21a of the vacuum tube 21 has a semi-spherical shape and is provided with anode material 25a. This embodiment has a radiation dose distribution which is similar to the radiation dose distribution of a radioactive implant seed, for example an Ir-192 implant seed. Therefore the embodiment as disclosed in FIG. 4c is highly suitable as a replacement for radioactive implant seeds for brachytherapy treatments.

In all three embodiments shown in FIGS. 4a–4c a getter material is electrically isolated accommodated within the hollow shaped cathode as explained above. Also with these three embodiments said getter material 30 eliminates or captures stray gas molecules still present in the cavity 17 of the vacuum tube 21, without being adversely affected by the high-voltage electric field established between the cathode 22 and anode 25. Therefore the use of the getter material guarantees a low vacuum level within the vacuum tube 21 necessary for a proper operation of the miniature X-ray source device according to the invention.

In a preferred embodiment the cathode is of a gated field emission type with a ferro-electric emitter allowing to control the electron flow more accurately independent of the accelerating high-voltage applied for generating the high-voltage electric field between the anode and the cathode.

Figure 5A:
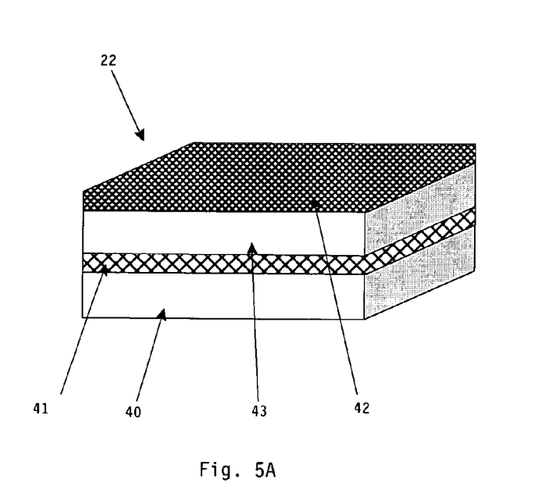
FIG. 5a–5c disclose further detailed views of a specific feature of a miniature X-ray source device according to the invention.

In FIG. 5a said ferro-electric electron emitting material 43 is positioned between a lower electrode 41 and an upper electrode 42, both electrodes being connected to said emitting means (see FIGS. 2a–2c). The whole assembly can be supported by a support or substrate 40.

By in applying a controlled voltage difference between the lower and upper electrodes 41, 42 of the cathode 22 the electron current from the ferro-electric material 43 towards the anode 25 can be modulated or even cut-off entirely. The driving voltage applied to the cathode depends on the state of the ferro-electric material, that is the crystal phase and the thickness thereof. The driving voltage for freeing electrons from the ferro-electric material decreases as the thickness of the cathode layer decreases. Furthermore the magnitude of the driving voltage is largely dependent on the size of the electron emitting region, that is the electron emitting whole size on the driving electrodes.

Figure 5B:
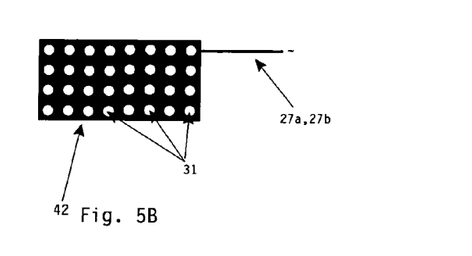

In order to further control and improve the free emission of electrons from the ferro-electric material 43 said upper electrode 42 is constructed as an electrically conductive sheet provided with a large number of openings 31. These openings 31 serve as emitting holes for the emitted free electrons. In FIG. 5b said specific embodiment of this feature is disclosed.

Figure 5C:
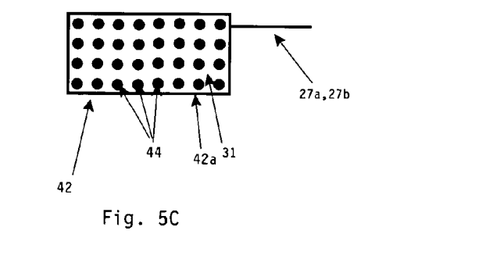

Another embodiment of this feature is shown in FIG. 5c, wherein said upper electrode 42 is constructed as an electrically conductive frame 42a in which a large number disc shaped elements 44 are fixed on said ferro-electric electron emitting material 43 (31). The exposed ferro-electric material 43 (indicated in FIG. 5c with reference numeral 31) is capable of emitting electrons.

Figure 6A:
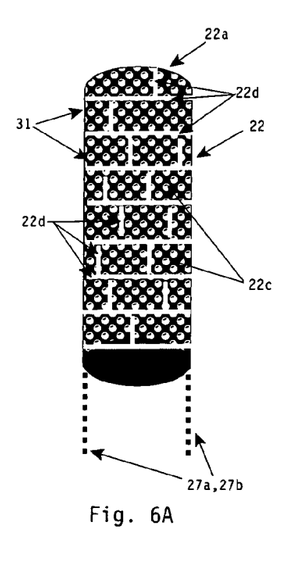
FIG. 6a–6c disclose three different embodiments of said specific feature as shown in FIGS. 5a–5c.
Figure 6B:
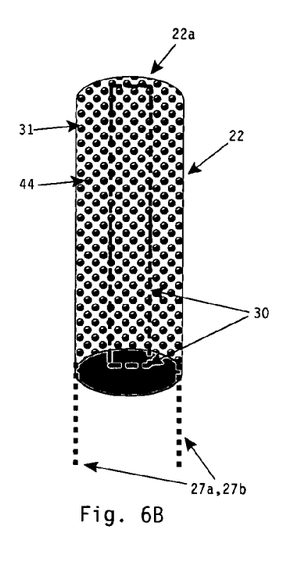
Figure 6C:
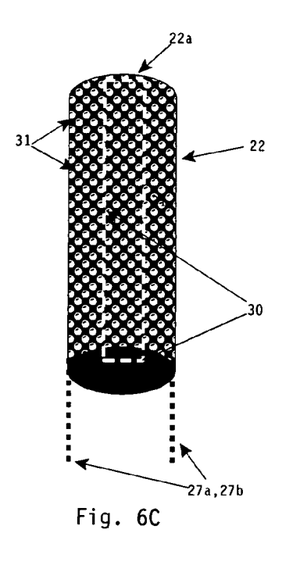

In FIGS. 6a–6c three advantageous embodiments of a cathode with shielding properties is disclosed. The cathode 22 is elongated having a polygonal shape.

In FIG. 6a the outer surface (the electron emitting surface) of the cathode 22 is provided multiple facets 22c with contact edges 22d. However also a hexagonal or octagonal or in general a polygonal surface are also possible. In a specific embodiment the electron emitting surface of the cathode can be subdivided in multiple facets with different contour shapes, which facets may or may be not interconnected with each other.

In FIGS. 6b and 6c the cathode 22 has a circular or oval cross section.

Furthermore the cathode 22 of FIG. 6a and 6c is of the ferro-electric emitting type as shown in FIGS. 5a and 5b, whereas in FIG. 6b the cathode 22 is of the ferro-electric emitting type as shown in FIGS. 5a and 5c.

With a miniature x-ray source according to the invention provided with a cathode of the ferro-electric emitter material type as explained above it will be able to produce x-rays on the complete surface of the tube in response to a pulsed electrical signal. Furthermore the advantage of such a cathode with ferro-electric emitter is the ability to control the electron flow and the X-ray dose rate independent of the accelerating voltage applied in the electric field.

This allows the miniature X-ray source device to be used for a variety of radiation treatment application including brachytherapy.

Figure 7A:
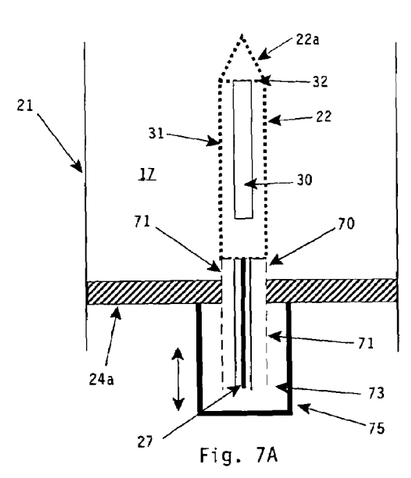
FIG. 7a–7b show a specific embodiment of a cathode for use in a miniature X-ray source device according to the invention using a crimp-off vacuum sealing technique.
Figure 7B:
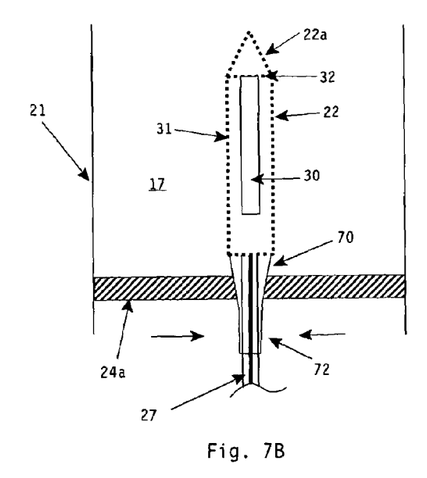

In FIGS. 7a–7b a further specific embodiment of a cathode to be used in a miniature X-ray source device according to the invention is disclosed.

In general a miniature X-ray source device having a vacuum chamber wherein an anode and cathode are accommodated, is manufactured by mounting the anode and cathode inside the vacuum chamber, closing the vacuum chamber, which chamber is subsequently vacuum pumped-down towards a desired vacuum level through a small orifice, which orifice is finally closed using a crimp-off technique or other closing method.

In WO 01/18842 it is disclosed to vacuum pump down and to close the X-ray vacuum cavity using a crimp-off technique, wherein the crimp-off joints are located at both longitudinal ends of the X-ray source device. The crimp-off joint of the anode is located at the frontal, distal end face of the miniature X-ray source device, wherein the crimp-off joint of the cathode has no other function than closing the orifice through which the cavity has been vacuum pumped-down.

The X-ray source devices disclosed in WO 01/18842 exhibit crimp-off joints enlarging the outer dimensions of the X-ray source device. Especially the crimp-off joint of the anode present at the frontal, distal end of the source device has a pointed constructional shape hampering the insertion of the X-ray source device into the patient, when introduced and advanced through a patient's lesion towards the location where a certain amount of X-ray radiation has to be administered.

In FIGS. 7a and 7b a further improvement of the known crimp-off vacuum tubes is disclosed. In FIG. 7a the cathode 22 is mounted on a support tube 70, which extends through the support member 24a. This support member 24a serves primarily as a vacuum sealing of the cavity 17 of the X-ray source device. Secondly it serves as a spacer for maintaining the cathode in place within the cavity.

The support tube 70 primarily serves as a support for the hollow, elongated cathode 22 and the getter material 30 contained in it. Secondly the support tube 70 serves as a pump-down connection with suitable vacuum pump means, which are shown schematically in FIG. 7a with reference numeral 75.

To this end the support tube 70 has an elongated hollow shape provided with a number of openings 71 connecting the inner cavity 17 of the vacuum chamber 21 through said openings 71 with the pump chamber 73 of the vacuum pump means 75. Through this pump connection the cavity 17 can be vacuum pumped-down towards a desired vacuum level necessary for a proper operation of the miniature X-ray source device.

Once the vacuum within the cavity 17 has reached or pumped down to its desired level said hollow support tube is crimped-off at the location 72 where the two arrows are situated in FIG. 7b. The crimp-off operation results in a vacuum tight closure joint 72 of the open connection between the cavity 17 and the outer atmosphere (reference numeral 73 in FIG. 7*a*).

As the single crimp-off joint is located near the cathode a significant reduction is obtained in the outer dimensions of the X-ray source device. Especially the drawbacks of a crimp-off joint at the distal end face of the X-ray source device are herewith avoided. Furthermore, the crimp-off joint 72 near the cathode 22 does not add to the outer dimensions of the X-ray source device as it is accommodated in the catheter tube (not shown) used to guide and transport the X-ray source device through a patient's lesion towards the location of radiation treatment.

More in particular the crimp-off joint 72 serves as an electrical connector for the co-axial high voltage cable 27 connecting the cathode 22 with a high voltage supply (not shown) for emitting free electrons from the cathode and/or for establishing said high-voltage electric field between the cathode 22 and the anode 25.

What is claimed is:

1. Miniature X-ray source device connected to a distal end of a guiding wire for insertion towards a desired location within an animal body for effecting radiation therapy, said X-ray source device at least comprising:
    a vacuum tube containing a cathode and an anode spaced apart at a distance from each other;
    emitting means for emitting free electrons from the cathode;
    electric field means for applying during use a high-voltage electric field between said cathode and said anode for accelerating said emitted free electrons towards said anode; and
    a getter material located in a high-voltage electric field free region in said vacuum tube and shielded from said high-voltage electric field by said cathode; wherein said vacuum tube being at least partly transparent to X-ray radiation emitted by said anode, characterized in that said cathode has a spatial construction surrounding said getter material, and wherein said getter material is supported by said cathode and electrically isolated therefrom.

2. Miniature X-ray source device according to claim 1, characterized in that said cathode is placed between said getter material and said anode.

3. Miniature X-ray source device according to claim 1, characterized in that said cathode is at least partly covering said getter material.

4. Miniature X-ray source device according to claim 1, characterized in that said cathode has an elongated shape with a polygonal cross-section and that said getter material is disposed within said cathode.

5. Miniature X-ray source device according to claim 4, characterized in that said elongated shaped cathode has a circular or oval cross-section.

6. Miniature X-ray source device according to claim 4, characterized in that said getter material is rod-shaped.

7. Miniature X-ray source device according to claim 1, characterized in that said cathode is provided with at least one opening.

8. Miniature X-ray source device according to claim 7, characterized in that said cathode is made from a grating material.

9. Miniature X-ray source device according to claim 1, characterized in that said cathode is of a gated field emission type having a ferroelectric electron emitting material.

10. Miniature X-ray source device according to claim 9, characterized in that said ferro-electric electron emitting material is positioned between a lower electrode and an upper electrode, both electrodes connected to a driving voltage.

11. Miniature X-ray source device according to claim 10, characterized in that said upper electrode is constructed as an electrically conductive sheet provided with a large number of openings serving as emitting holes for the emitted free electrons.

12. Miniature X-ray source device according to claim 10, characterized in that said upper electrode is constructed as at least one electrically conductive frame in which a large number disc shaped elements partly is fixed on ferro-electric electron emitting material.

13. Miniature X-ray source device according to claim 1, characterized in that said cathode is of a cold cathode type formed from carbon nanotubes.

14. Miniature X-ray source device according to claim 13, characterized in that said carbon nanotubes are aligned mono-wall nanotubes.

15. Miniature X-ray source device according to claim 13, characterized in that said carbon nanotubes are aligned multi-wall nanotubes.

16. Miniature X-ray source device according to claim 13, characterized in that said carbon nanotubes are randomized nanotubes.

17. Miniature X-ray source device according to claim 1, characterized in that said vacuum tube comprises a distal end face, the inner surface of said distal end face also being provided with said anode material, and wherein a part of said electron emitting material of said cathode is facing said distal end face.

18. Miniature X-ray source device according to claim 17, characterized in that said cathode is tubular shaped having a distal free end provided with electron emitting material directed towards said distal end face of said vacuum tube.

19. Miniature X-ray source device according to claim 17, characterized in that said electron emitting surface of said cathode conforms to the inner surface of said vacuum tube being covered with said anode material.

20. Miniature X-ray source device according to claim 17, characterized in that said distal end face of said vacuum tube and said distal free end of said cathode are semi-spherically shaped.

21. Miniature X-ray source device according to claim 17, characterized in that said distal end face of said vacuum tube and said distal free end of said cathode are equally spaced apart from each other.

22. Miniature X-ray source device connected to a distal end of a guiding wire for insertion towards a desired location within an animal body for effecting radiation therapy, said X-ray source device at least comprising:
    a vacuum tube containing a cathode and an anode spaced apart at a distance from each other;
    emitting means for emitting free electrons from the cathode;
    electric field means for applying during use a high-voltage electric field between said cathode and said anode for accelerating said emitted free electrons towards said anode;
    a getter material located in a high-voltage electric field free region in said vacuum tube; wherein
    said vacuum tube being at least partly transparent to X-ray radiation emitted by said anode, characterized in that said cathode is arranged for shielding said getter material from said high-voltage electric field and character ized in that said cathode is supported by a hollow support tube with one end extending within the vacuum chamber and with the other end extending outside the vacuum chamber, which other end is subjected to a crimp-off operation for sealing the vacuum chamber.

23. Miniature X-ray source device according to claim 22, characterized in that said hollow support tube is provided with multiple openings present in its circumferential surface.

24. Miniature X-ray source device according to claim 22, characterized in that said crimped-off other end of the support tube serves as an electrical connection between the cathode and the emitting means for emitting free electrons from the cathode and/or the electric field means.

* * * * *